United States Patent [19]

Zhu et al.

[11] Patent Number: 5,399,680

[45] Date of Patent: Mar. 21, 1995

[54] RICE CHITINASE PROMOTER

[75] Inventors: Qun Zhu; Christopher J. Lamb, both of San Diego, Calif.

[73] Assignee: The Salk Institute for Biological Studies, La Jolla, Calif.

[21] Appl. No.: 704,288

[22] Filed: May 22, 1991

[51] Int. Cl.⁶ ............... C12N 15/11; C12N 15/82; C12N 5/04; A01H 5/00
[52] U.S. Cl. ............... 536/24.1; 435/69.1; 435/91.3; 435/177.3; 435/240.4; 800/205
[58] Field of Search ............. 536/27, 23.6, 24.1; 435/172.3, 69.1, 91, 240.4, 91.3; 800/205; 935/6, 35, 47

[56] References Cited

FOREIGN PATENT DOCUMENTS

WO8912059 12/1989 WIPO ................. C07H 15/12

OTHER PUBLICATIONS

Huang, J. K. et al. 1991, *Plant Mol. Biol.*, vol. 16 pp. 479–480.
Roby, D. et al. 1990 *Plant Cell*, vol. 2, pp. 999–1007.
Bol, J. F. et al. 1990, *Annu. Rev. Phytopathol.*, vol. 28 pp. 113–138.
Broglie, K. E. et al. 1986 *Proc. Natl. Acad. Sci. USA*, vol. 83 pp. 6820–6824.
Broglie, K. E. et al. 1989 *Plant Cell*, vol. 1 pp. 599–607.
Swegle, M. et al., 1989 *Plant Mol. Biol.*, vol. 12 pp. 403–412.
Zhn, Q. et al. 1991 *Mol. Gen. Genet.*, vol. 226 pp. 289–296.
Nishizawa, Y. et al. 1991 *Plant Science*, vol. 76, pp. 211–218.
Kaulen et al., Light–induced expression of the chimeric chalcone synthase–NPTII gene in tobacco cells, EMBO Journal vol. 5:1–8 (1980).
Hahlbrock et al., Rapid Response of Suspension–cultured Parsley Cells to the Elicitor from *Phytophthora megasperma* var. *sojae*, Plant Physiology vol. 67:768–773 (1981).
Darnell, Variety in the level of gene control in eukaryotic cells, Nature vol. 297:365–371 (1982).
Kuhn et al., Induction of phenylalanine ammonia–lyase and 4–coumarate:CoA ligase mRNAs in cultured plant cells by UV light or fungal elicitor, Proceedings of the National Academy of Science USA vol. 81:1102–1106 (1984).
Ryder et al., Elicitor rapidly induces chalcone synthase mRNA in *Phaselous vulgaris* cells at the onset of the phytoalexin defense response, Proceedings of the National Academy of Science USA vol,. 81:5724–5728 (1984).
Jones, Phenylalanine Ammonia–lyase: Regulation of its Induction and its Role in Plant Development, Phytochemistry 23:1349–1359 (1984).

*Primary Examiner*—David T. Fox
*Assistant Examiner*—Mary E. Mosher
*Attorney, Agent, or Firm*—Pretty, Schroeder, Brueggemann & Clark, Stephen E. Reiter, Robert T. Ramos

[57] ABSTRACT

Novel chitinase gene, and its associated regulatory region, from a monocotyledon plant is described.

13 Claims, 6 Drawing Sheets

FIG. 1A

```
              10                    30                                50
RICE     MRALAVVAMVARPF.....LAAAVHAEQCGSQAGGAVCPNCLCCSQFGWCGSTSDYCGAG
TOBACCO         ......SL    LLSAS            R ASG         K    N N  P
POTATO1         ...TIFSLLFSLL              LN SGSN..VVHRPD L APG  K    N N  P
POTATO2         RHKE NF YLLFSLLV VS AL QN    G KA ASGQ      K    N N  S
BEAN            IWSVG  W L....L          VGGSYG  R     L  GGN         T    P 70                    90                                110
RICE     .CQSQCSRLRRRRPDASGGGGSGVASIVSRSLFDLMLLHRNDAACPA.SNFYTYDAFVAA
TOBACCO  N P........GGPTPP  GDLG   I S M  Q  K      N QG KG   S N   IN
POTATO1  N P........GGP PSGDLGGVI N M  Q  N      N QGKN       S N   IS
POTATO2  N P........GGGPGP P GDLG AI N M  Q  K      ENS QG K        S N   IN
BEAN              .........GGPSPAPTDLSALI  T  Q  K       G     KG        I 130                   150                               170
RICE     ASAFPGFAAAGDADTNKREVAAFLAQTSHETTGGWATAPDGPYTWGYCFKEENGGAGPDY
TOBACCO  RS  GTS  TTAR    I F                     A    WLR Q SP .
POTATO1  GS  GTT  ITAR    I                   PS  A    LR Q SP .
POTATO2  RS  GTS  INAR    I F                 S   A    LR R NP .
BEAN     K Y S GNT TA R    I G                    A    VR RNPST..
```

```
                  190                          210                         230
RICE      CQQSAQWPCAAGKKYYGRGPIQLSYNFNYGPAGGAIGADLLGDPDLVASDATVSFDTAFW
TOBACCO   TP  G       P  R  F          I H Y   C R   V     NN     T PVI  KS L
POTATO1   TP  S       P  R  F          I H Y   C R   V     NN     T SVI  KS I
POTATO2   PP  S       P  R  F          I H Y   C R   AV    NN     T PVI  K  L
BEAN      SATP F    P QQ                 W Y   QC R   V    NK     T SVI  KS L 250                          270                         290
RICE      FWMTPQSPKPSCNAVATGQWTPSADDQRAGRVPGYGVITNIINGGLECGHGEDDRIADRI
TOBACCO              HD II R Q       SA RA N L   F                      R T S  VQ
POTATO1              HD I  R Q       GA  A N     F                      S S    VQ
POTATO2              HD II R N       SA RA N L   F                      R T N  VQ
BEAN              A  SHD I  SR       SA VA R L  TV                      R Q S  VQ 310                          330
RICE      GFYKRYCDILGVSYGANLDCYSQRPSAPP....KLRLPSFHTVINNH*
TOBACCO   R   S      P  D    GN  SFGNGLLVDTM*
POTATO1   R   G      P  D    GN  SFGNG     L ....VD    *
POTATO2   R   S      TP D    VN  WFGNALL   ..VDTL*
BEAN      F   L      G  N    T FGNS        L . SDLV SQ*

```
                    HEVEIN DOMAIN                        SPACER              CATALYTIC DOMAIN

HEVEIN  EQCGRQAGGKLCPNNLCCSQWGCGSTDEYCSPDHNCQSNCKD
WIN1    Q           K  A  SG           FG   P F  SQG    R TG
WIN2    Q           R  A  G            FG   S P  SQG    O TG
WGA    -K  S S                      GS LGS F --GGG      GACS
RICE       S        AV C              FG   SD GAG---    Q SRIRRRRPDASGGGGSGVASIVSRSLFDLMLL
BEAN                A  GGN            FG   TD G---      Q -GGPSPAP----TDLSALI-SRSTFDQMLK
BASIC      S        AR SG            KFG   ND G-        Q PGGPTPTPPPGGGDLGSII-SSSMFDQMLK
PR-Q                                                                  QGIGS-IVTSDLFNEMLK
PR-P                                                                  QGIGS-IVTNDLFNEMLK
```

RICE CHITINASE PROMOTER

The present invention relates to regulatory elements functional in plants, especially monocotyledons. In addition, the present invention relates to novel plant genes encoding products involved in plant defense.

BACKGROUND OF THE INVENTION

The response of plants to microbial attack involves de novo synthesis of an array of proteins designed to restrict the growth of the pathogen. These proteins include hydroxyproline-rich glycoproteins, proteinase inhibitors, enzymes for the synthesis of phytoalexins, enzymes contributing to the reinforcement of cell walls, and certain hydrolytic enzymes such as chitinase and glucanase.

Plant defenses can also be activated by elicitors derived from microbial cell walls and culture fluids. In dicotyledonous plants, extensive studies have shown that microbial attack or elicitor treatment induces the transcription of a battery of genes encoding proteins involved in these defense responses, as part of a massive switch in the overall pattern of gene expression. The functional properties of the promoters of several of these dicotyledonous defense genes have been characterized. In contrast, relatively little is known about the inducible defenses in monocotyledonous plants, including the major cereal crops. For example, the transcriptional regulation of defense genes from monocotyledonous plants has not been examined.

Chitinase (EC 3.2.1.14) catalyzes the hydrolysis of the $\beta$-1,4 linkages of the N-acetyl-D-glucosamine polymer chitin. Chitin does not occur in higher plants, but is present in the cell walls of many fungi. Chitinase, which exhibits complex developmental and hormonal regulation, has been found in many species of higher plants. In addition, chitinase activity is markedly increased by wounding, ethylene, or microbial elicitors. Furthermore, chitinase is involved in the hypersensitive resistance response to microbial attack. Purified plant chitinase attacks and partially digests isolated cell walls of potentially pathogenic fungi. It is this latter enzyme activity, rather than chitin-binding lectin activity, that is responsible for the inhibition of fungal growth. Chitinase and $\beta$-glucanase exhibit synergistic antifungal activity in vitro. A number of pathogenesis-related proteins (also referred to as "PR proteins") have been found to be chitinases or glucanases.

Chitinase genes from a number of dicotyledonous plants (including bean, cucumber, potato, and tobacco) have been isolated and characterized.

Plant chitinases can be divided into at least three classes, based on amino acid sequence and cellular localization. Class I chitinases are basic isoforms which are structurally homologous and are primarily localized in the central vacuole. Basic chitinases contain a catalytic domain, and a cysteine-rich domain similar to rubber hevein. The hevein domain is thought to serve as an oligosaccharide-binding site. There is a variable spacer region between the hevein and the catalytic domains.

Class II chitinases are usually found in the extracellular fluid of leaves and in the culture medium of cell suspensions, suggesting that they are localized in the apoplastic compartment, consistent with a major function in defense. This hypothesis is supported by recent observations that some PR proteins are acidic chitinases.

Class III chitinases, such as a recently described cucumber chitinase, show no homology with either Class I or Class II chitinases, but are homologous to a lysozyme/chitinase from *Parthenocissus quinquifolia*. Class III chitinases are located in the extracellular compartment.

While chitinases from dicotyledons have been well characterized, and many of the corresponding genes have been isolated, there is little information available on the structure and expression of chitinase genes from monocotyledons.

SUMMARY OF THE INVENTION

In accordance with the present invention, we have isolated and characterized a monocotyledon chitinase gene and its associated regulatory sequences. The regulatory sequences of the invention are highly expressed in certain floral organs, and are highly inducible from a low basal level of expression upon exposure to plant defense elicitors.

The regulatory sequences of the invention are useful, for example, for the controlled expression of a wide variety of gene products, such as reporter constructs, functional proteins (e.g., enzymes), and the like.

BRIEF DESCRIPTION OF THE DRAWINGS

FIG. 1 presents a comparison of the amino acid sequences of the invention chitinase (derived from rice) SEQ ID NO. 3 with the amino acid sequences of basic chitinases from dicotyledon plants. The predicted amino acid sequence of RCH10 is shown on the top line, while amino acid sequences of tobacco, SEQ ID NO. 6 potato, SEQ ID NO. 7-8 and bean SEQ ID NO. 9 basic chitinases are aligned with the RCH10 sequence. Only amino acids differing from the RCH10 sequence are shown. "Dots" indicate gaps in the sequence comparison; while an "*" indicates a stop codon.

FIG. 2 presents a comparison of the amino acid sequence of the RCH10 hevein domain with the amino acid sequences of the hevein domains Sequence ID No. 3 (amino acid residues 22-92), of other proteins, i.e., rubber hevein SEQ ID NO. 10 [amino acid residues 1-43; see Lucas et al., FEBS Lett. 193: 208-210 (1985)], potato WIN1 SEQ ID NO. 11 and WIN2 SEQ ID NO. 12 [amino acid residues 26-68 of each; see Stanford et al., Mol. Gen. Genet. 215: 200-208 (1989)], wheat germ agglutinin isolectin SEQ ID NO. 13 [WGA, amino acid residues 88-127; see Wright et al., Biochemistry 23:280-287 (1984)], rice RCH10 SEQ ID NO. 3 (amino acid residues 22-92), bean basic chitinase SEQ ID NO. 14 [amino acid residues 1-79; see Broglie et al., Proc. Natl. Acad. Sci. USA 83: 6820-6824 (1986)], tobacco basic chitinase SEQ ID NO. 15 (amino acid residues 1-87); tobacco PR-P SEQ ID NO. 17 and PR-Q SEQ ID NO. 16 proteins (amino acid residues 25-57 of each) [see Payne et al., Proc. Natl. Acad. Sci. USA 87:98-102 (1990) with respect to each of the tobacco sequences]. Each of the above sequences were aligned to maximize sequence identity; only amino acids which differ from the rubber hevein sequence are set forth in the Figure.

FIG. 3 summarizes expression results with RCH10-GUS gene fusions in transgenic tobacco plants.

FIG. 4 presents the kinetics of wound and elicitor induction of RCH10-GUS gene fusions in transgenic tobacco leaves.

DETAILED DESCRIPTION OF THE INVENTION

Figure 3A:
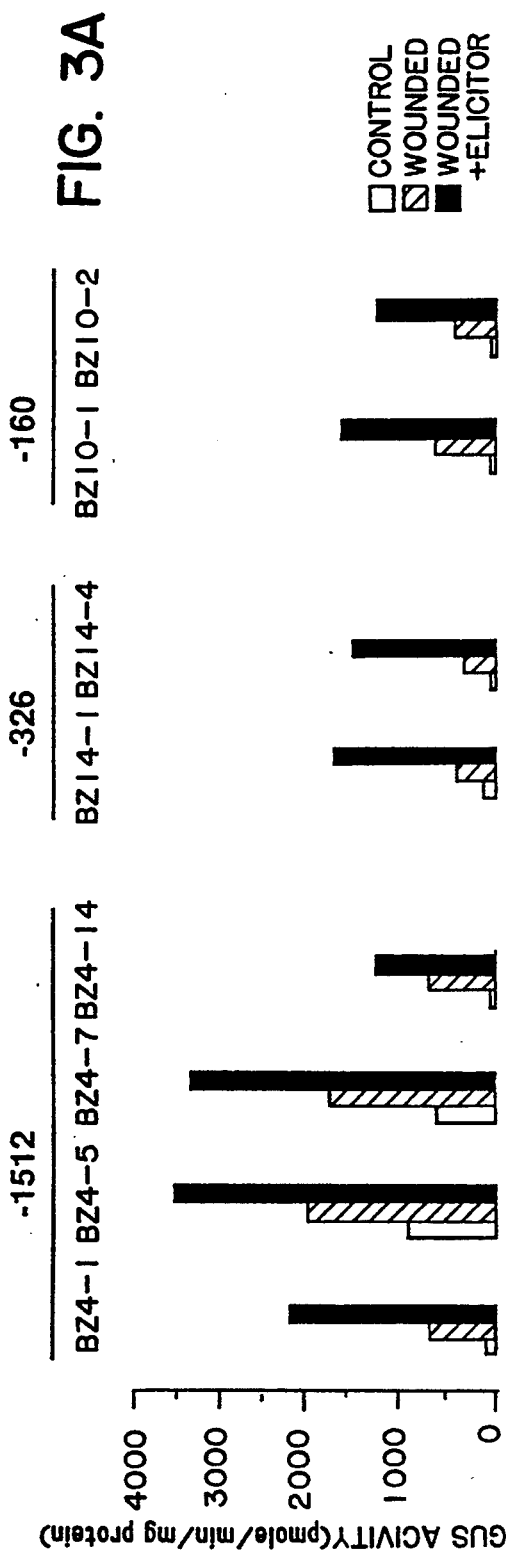
FIG. 3A deals with wound and elicitor induction in leaf tissue.

In accordance with the present invention, there is provided a DNA fragment comprising a monocotyledon promoter characterized as being responsive to physical and/or biological stress; wherein said DNA fragment is further characterized by the following relative pattern of expression in mature plants:
  a low level of expression in leaves;
  a moderate level of expression in plant stems; and
  the highest level of expression in the plant roots and in the male and female parts of plant flowers.

In accordance with another embodiment of the present invention, there are provided DNA construct(s) comprising the above-described monocotyledon promoter, operatively linked to at least one structural or functional gene, e.g., a reporter gene.

In accordance with yet another embodiment of the present invention, there is provided plant material transformed with the above-described DNA construct(s).

In accordance with still another embodiment of the present invention, there is provided a method for inducing the expression of heterologous, functional gene(s) in monocotyledon and dicotyledon plants, said method comprising:
  subjecting the above-described plant material to conditions which induce transcription of said DNA construct(s).

In accordance with a further embodiment of the present invention, there are provided substantially pure proteins having in the range of about 300 up to 350 amino acids, characterized by:
  a hevein domain having in the range of about 40 up to 80 amino acids, wherein said hevein domain is about 70% homologous with respect to dicotyledonous chitinase hevein domains;
  a glycine- and arginine-rich spacer region having in the range of about 6 up to 12 amino acids; and
  a catalytic domain having in the range of about 240 up to 280 amino acids, wherein said catalytic domain is about 77% homologous with respect to dicotyledenous chitinase catalytic domains.

Proteins of the present invention can optionally further comprise a signal peptide having in the range of about 16 up to 30 amino acids.

A presently preferred protein of the invention has about 336 amino acids, wherein:
  the hevein domain has about 40 amino acids;
  the glycine- and arginine-rich spacer region has about 12 amino acids; and
  the catalytic domain has about 262 amino acids.

This presently preferred peptide will optionally have a signal peptide of about 21 amino acids.

In accordance with a still further embodiment of the present invention, there are provided DNA sequences encoding the above-described protein, optionally further containing a readily detectable label.

In accordance with yet another embodiment of the present invention, there is provided a method for the identification of novel chitinase genes, said method comprising
  probing a nucleic acid library with at least a portion of the above-described labeled DNA under suitable hybridization conditions, and
  selecting those clones of said library which hybridize with said probe.

The DNA fragment comprising a monocotyledon promoter contemplated by the present invention is responsive to physical and/or biological stress. As used herein, the term "responsive to physical and/or biological stress" refers to DNA sequences which are responsive to exposure to physical stress, such as, for example, wounding (e.g., tearing, folding, bending, and the like), bruising, and the like; or to biological stress, such as, for example, plant defense elicitors (e.g., the high molecular weight fraction heat-released from the cell walls of the soybean fungal pathogen *Phytophthira megasperma* f. sp. *glycinea*, purified glucan elicitors, and the like); and so forth.

The relative expression pattern of peptides maintained under the expression control of the invention monocotyledon promoter in mature plants is typically as follows:
  a low level of expression in leaves;
  a moderate level of expression in plant stems; and
  the highest level of expression in the plant roots and in the male and female parts of plant flowers.

The monocotyledon promoter of the present invention can be further characterized by reference to the sequences set forth in the Sequence Listing provided herewith, referring specifically to Sequence ID No. 1 (and Sequence ID No. 2). For example, a DNA fragment having substantially the same sequence as nucleotides 1836 to 1884, as set forth in Sequence ID No. 1, is operative to confer responsiveness to physical and/or biological stress on a gene associated therewith. Of course, those of skill in the art recognize that longer fragments from the upstream portion of the invention chitinase gene can also be used, such as, for example, a DNA fragment having substantially the same sequence as nucleotides 1810 to about 1884, as set forth in Sequence ID No. 1; a DNA fragment having substantially the same sequence as nucleotides 1724 to about 1884, as set forth in Sequence ID No. 1; a DNA fragment having substantially the same sequence as nucleotides 1558 to about 1884, as set forth in Sequence ID No. 1; a DNA fragment having substantially the same sequence as nucleotides 372 to about 1884, as set forth in Sequence ID No. 1; a DNA fragment having substantially the same sequence as nucleotides 1 to about 1884, as set forth in Sequence ID No. 1; and the like.

In addition, sequences downstream of the transcription start site can also be included in the regulatory elements employed herein (up to about 100 or more nucleotides derived from downstream of the transcription start site can be employed). Thus, the above-described regulatory elements can be extended to comprise, for example, nucleotides 1–76 as set forth in Sequence ID No. 2, thereby forming regulatory constructs such as:

a contiguous sequence of nucleotides comprising nucleotides 1836 to 1884, as set forth in Sequence ID No. 1, plus nucleotides 1-76 as set forth in Sequence ID No. 2;

a contiguous sequence of nucleotides comprising nucleotides 1810 to 1884, as set forth in Sequence ID No. 1, plus nucleotides 1-76 as set forth in Sequence ID No. 2;

a contiguous sequence of nucleotides comprising nucleotides 1724 to 1884, as set forth in Sequence ID No. 1, plus nucleotides 1-76 as set forth in Sequence ID No. 2;

a contiguous sequence of nucleotides comprising nucleotides 1558 to 1884, as set forth in Sequence ID No. 1, plus nucleotides 1-76 as set forth in Sequence ID No. 2;

a contiguous sequence of nucleotides comprising nucleotides 372 to 1884, as set forth in Sequence ID No. 1, plus nucleotides 1-76 as set forth in Sequence ID No. 2;

a contiguous sequence of nucleotides comprising nucleotides 1 to 1884, as set forth in Sequence ID No. 1, plus nucleotides 1-76 as set forth in Sequence ID No. 2;

and the like.

The monocotyledon promoter of the present invention can be used for the controlled expression (with respect to both spatial and temporal expression) of a wide variety of gene products. For example, promoter plus reporter constructs (e.g., wherein said reporter gene is selected from chloramphenicol acetyltransferase, β-glucuronidase, β-lactamase, firefly luciferase, and the like) can be used to monitor when and where expression from the invention promoter is induced in a host plant or plant cell.

Alternatively, constructs comprising the monocotyledon promoter of the present invention, plus structural gene, can be employed for the controlled expression of numerous structural (or functional) genes, such as, for example, the *Bacillus thuringensis* toxin gene, genes encoding enzymes involved in phytoalexin biosynthesis, proteinase inhibitor genes, lytic enzyme genes, genes encoding inducers of plant disease resistance mechanisms, and the like.

Plants contemplated for use in the practice of the present invention include both monocotyledons and dicotyledons. Monocotyledons are presently preferred because the invention monocotyledon promoter is expected to be functional in nearly all monocotyledons, whereas dicotyledon promoters have frequently been non-operative when used in monocotyledon hosts. Conversely, it is expected that the invention monocotyledon promoter(s) will be functional in many dicotyledon hosts.

Exemplary monocotyledons contemplated for use in the practice of the present invention include rice, wheat, maize, sorgham, barley, oat, forage grains, as well as other grains.

Plants or plant cells containing the above constructs (introduced by standard techniques, such as, for example, by transfection) can be used to study patterns of development, for the controlled expression of various plant defense genes, for the expression of selectable marker genes (to screen for mutants or compounds that modulate stress signal transduction pathways), and the like.

In accordance with one embodiment of the present invention, the rice chitinase structural gene has also been isolated and characterized. This gene is characterized as having only coding sequence (i.e., contains no introns), and encodes the above-described polypeptide, plus signal sequence. The rice chitinase structural gene can be further characterized as having substantially the same nucleic acid sequence as nucleotides +55 through +1062, as set forth in Sequence ID No. 2.

The rice chitinase gene of the present invention encodes a novel protein, i.e., rice basic chitinase. The rice basic chitinase of the present invention can be further characterized as having substantially the same amino acid sequence as amino acids 22-357, as set forth in Sequence ID Nos. 2 and 3 (for the mature form of rice basic chitinase) or amino acids 1-357, as set forth in Sequence ID Nos. 2 and 3 (for the precursor-form of rice basic chitinase).

Optionally, the rice chitinase structural gene, or a fragment of at least 100 contiguous nucleotides thereof, can be labeled (wherein said label is selected from a radiolabeled molecule, a fluorescent molecule, a chemiluminescent molecule, an enzyme, a ligand, a toxin, a selectable marker, etc). The resulting labeled rice chitinase structural gene (or a portion thereof) can be used, for example, as a probe (e.g., as part of a method to identify additional monocotyledon or dicotyledon chitinase-like genes), and the like.

One of skill in the art can readily determine suitable hybridization conditions for screening libraries in search of additional monocotyledon or dicotyledon chitinase-like genes. For example, one would preferably use stringent hybridization conditions when screening for other monocotyledon chitinase or chitinase-like genes; while one would likely use milder hybridization conditions when screening for dicotyledon chitinase or chitinase-like genes. Stringent hybridization conditions comprise a temperature of about 42° C., a formamide concentration of about 50%, and a moderate to low salt concentration. More mild hybridiation conditions comprise a temperature below 42 ° C., formamide concentrations somewhat below 50%, and moderate to high salt concentrations. Exemplary mild hybridization conditions comprise a temperature of about 37° C., a formamide concentration of about 20%, and a salt concentration of about 5X standard saline citrate (SSC; 20X SSC contains 3M sodium chloride, 0.3M sodium citrate, pH 7.0). Such conditions will allow the identification of sequences which have a substantial degree of similarity with the probe sequence, without requiring perfect homology for the identification of a stable hybrid. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe.

In the invention method for inducing gene expression in monocotyledon (and dicotyledon) plants, plant material containing DNA constructs under the expression control of invention monocotyledon regulatory sequences is subjected to conditions which induce transcription of the DNA construct. Such conditions include exposing the plant or plant material to physical stress (e.g., wounding) and/or biological stress (e.g., infection, elicitor molecules derived from pathogens).

The invention will now be described in greater detail by reference to the following non-limiting examples.

EXAMPLES

Nucleotide sequences were determined by the dideoxy chain-termination [Sanger et al., PNAS 74: 5463–5467 (1977)]. Fragments for sequencing were obtained by restriction endonuclease digestion or exonuclease III deletion [Ausubel et al., Current Protocols in Molecular Biology, Wiley, N.Y. (1987)].

EXAMPLE I

Plant Material

Rice (*Oryza sativa* L. cv. IR36) seeds were sterilized in 70% ethanol for 2 minutes and then in a 2% solution of sodium hypochlorite for 30 minutes. Sterilized seeds were germinated and grown in MS medium (without hormones) in darkness [Murashige and Skoog, Physiol. Plant 15: 473–497 (1962)]. Two weeks after germination, leaves, roots and stems were harvested separately, then immediately frozen in liquid nitrogen and stored at −80° C. until required. Rice (cv. CR76) cell suspension cultures were grown in N6 medium [Chu et al., Scientia Sinica 5: 659–668 (1975)] and maintained in darkness. The high molecular weight fraction heat-released from mycelial cell walls of *Phytophthora megasperma* pv. *glycinea* (Pmg) was used as elicitor [Sharp et al., J. Biol. Chem. 259: 11321–11326 (1984)]. Elicitation experiments were conducted on 5-day-old cultures, the stage of the cell culture cycle during which maximum responsiveness to elicitor was observed.

EXAMPLE II

DNA and RNA Isolation

Genomic DNA from rice cell suspension cultures was prepared according to the method of Ausubel et al., supra. DNA was isolated from tobacco leaves as described by Schmid et al., Plant Cell 2: 619–631 (1990). Plasmid and phage DNA were isolated by standard methods [Maniatis et al., Molecular Cloning: A laboratory manual, Cold Springs Harbor Laboratories, Cold Spring Harbor, N.Y. (1982)]. RNA from cell suspension cultures and plant tissues was prepared by the guanidinium isothiocyanate method [Chomczynski and Sacchi, Anal. Biochem. 162:156–159 (1989)].

EXAMPLE III

Isolation and Characterization of Genomic Rice Clones

A lambda-DASH library containing 15–25 kb genomic fragments from a Sau3A partial digest of rice genomic DNA was a gift from N. H. Chua. pCht12.3, a 650 bp bean basic chitinase cDNA fragment cloned in pBluescript, was used as probe [Hedrick et al., Plant Physiol. 86:182–186 (1988)]. For library screening, filters were pre-hybridized for 2–4 hours at 42° C. in 30% formamide, 5×Denhardt's solution (1×Denhardt's solution is 0.02% bovine serum albumin, 0.02% Ficoll, and 0.02% polyvinylpyrrolidone), 5×SSC (1×SSC is 0.15M NaCl, 15 mM sodium citrate), and 100 μg of sheared salmon sperm DNA per ml. The filters were then hybridized for 24 hours at 42° C. in the same buffer with nick-translated probe DNA. Filters were washed in 2×SSC, 2% SDS at 42° C. for 30 minutes and autoradiographed at −80° C. Purified phage clones containing chitinase sequences were analyzed by restriction endonuclease digestion and Southern blot hybridization. Selected restriction fragments were subcloned into pGEM7 or pBluescript vector.

EXAMPLE IV

DNA Blot Hybridization

Rice genomic DNA samples were digested with various restriction enzymes, fractionated by electrophoresis on a 1% agarose gel and blotted onto a nylon membrane (Genescreen plus). Hybridization to genomic DNA was performed for 24 hours at 65° C. in 1% SDS, 1M NaCl, 10% dextran sulfate, 100 μg per ml sheared, denatured salmon sperm DNA, and the DNA probe labeled with [$^{32}$P]. The membrane was washed with constant agitation, twice in 2×SSC for 5 minutes at room temperature and once in 2×SSC, 1% SDS for 45 minutes at 65° C.

Genomic Southern blots with tobacco DNA were probed with the HindIII/SacII fragment of pBI101 containing GUS coding sequences using standard procedures.

EXAMPLE V

RNA Blot Hybridization

RNA samples were separated by electrophoresis on a 1% agarose formamide gel in 1×3-[N-morpholino]propanesulfonic acid (MOPS)/EDTA buffer (10×MOPS/EDTA buffer is 0.5M MOPS, pH 7.0, 0.01M EDTA, pH 7.5), and blotted onto a nylon membrane. Before hybridization, the membranes were baked at 80° C. for 2 hours. The same hybridization conditions as in Southern blot analysis were used, except that hybridization was at 60° instead of 65° C.

EXAMPLE VI

Fusion Protein Analysis

A 941 bp fragment from the chitinase RCH10 coding region (positions +85 to +1026 relative to the transcription start site; nucleotides 85-1026, see Sequence ID No. 2) was inserted into pRX-1, pRX-2, and pRX-3 expression vectors [Rimm and Pollard, Gene 75: 323–327 (1989)] to generate pBZ7-1, pBZ7-2, and pBZ7-3, respectively. These plasmids were transferred into *Escherichia coli* strain HB101 by the $CaCl_2$ method [Maniatis et al. supra], and the transformed cells grown to stationary phase at 37° C. in LB broth. The cells were then inoculated into 5 ml of M9-CA minimal medium containing 100 μg/ml ampicillin, grown for 3 hours at 37° C., and then induced by addition of indolylacrylic acid to a final concentration of 10 μg/ml. After 5 hours, the cells were harvested and lysed by sonication in 10 mM TRIS-HCl, pH 8.0, 50 mM EDTA, 8% sucrose, 0.5% Triton X-100, and lysozyme (2 mg/ml). Soluble bacterial extracts were analyzed in a 10% SDS-polyacrylamide gel [Maniatis et al. supra]. Immunoblotting was performed as described by Bradley et al., Planta 173:149–160 (1988). Antiserum to bean chitinase, prepared employing standard techniques, was obtained as a gift from T. Boller.

EXAMPLE VII

Isolation and Nucleotide Sequence of RCH10

A rice genomic library was screened using as a probe the insert of pCht12.3, which contains cDNA sequences of a bean basic chitinase [Hedrick et al., supra]. From 12 plaque-purified clones, 3 positive clones were characterized by restriction mapping and Southern blot hybridization. A 2.5 kb HindIII fragment from one of these clones, designated RCH10, was subcloned. Nucleotide sequencing showed that this fragment contained a 1.0 kb open reading frame (ORF), together with 1.5 kb of upstream sequence. Subcloning of two HincII fragments that overlapped the HindIII fragment gave an additional 372 bp of nucleotide sequence 5' of the HindIII fragment and 125 bp 3' of this fragment. This 3.0 kb sequence contained the complete RCH10 chitinase gene (see Sequence ID No. 1).

A single long ORF with no introns encoded a polypeptide of 336 amino acids (see FIG. 1 and Sequence ID No. 2). FIG. 1 shows the primary structure of the RCH10 gene product compared with basic chitinases from dicotyledon plants. The RCH10 polypeptide contains a hydrophobic putative signal peptide of 21 amino acids at the N-terminus, as well as hevein and catalytic domains. The hevein domain of RCH10 is about 40 amino acids long and is cysteine-rich. FIG. 2 shows a comparison of the hevein domain of RCH10 with the hevein polypeptide and other gene products containing this domain, including WIN1, WIN2, and wheat germ agglutinin isolectin. The hevein domain of RCH10 shares about 70% amino acid sequence identity with these other hevein domains. The hevein domain and catalytic domain of RCH10 are separated by a glycine- and arginine-rich spacer region. The amino acid sequence identity between the RCH10 catalytic domain and the catalytic domains of chitinases from dicotyledons is about 77%.

EXAMPLE VIII

TrpE-RCH10 Fusion Protein

The level of similarity between RCH10 and basic (class I) chitinase genes from dicotyledons strongly suggests that RCH10 encodes a rice chitinase. To confirm the identity of the protein product encoded by the RCH10 gene, a fragment from the coding region (positions +85 to +1026) was inserted into the E. coli expression vectors pRX1, pRX2, and pRX3 to obtain the plasmids pBZ7-1, pBZ7-2, pBZ7-3. pBZ7-1 codes for a fusion polypeptide consisting of 18 amino acids from TrpE, 3 amino acids from the linker sequence, and 314 amino acids from the chitinase gene fused in the same reading frame. pBZ7-2 and pBZ7-3 are respectively 1 and 2 bases out of frame compared to pBZ7-1. These three plasmids were transferred into E. coli strain HB101, and soluble bacterial extracts were separated in a 10% SDS-poly-acrylamide gel and stained with Coomassie blue. The results showed an additional 37.5 kDa polypeptide in the cells transformed with pBZ7-1, whereas no additional polypeptides were detected in cells transformed with pBZ7-2 or pBZ7-3. Western blot analysis showed that the 37.5 kDa species in cells transformed with pBZ7-1 reacted with antiserum to bean chitinase, confirming that the RCH10 gene encodes a rice chitinase.

EXAMPLE IX

Transcription Start Site

The transcription start site was determined by primer-extension analysis using a synthetic 28-mer oligonucleotide identical to the sequence of the antisense DNA strand at residues 132-104 downstream from the translational initiation codon (SEQ ID NO: 4) (5'-CCG-AAC-TGG-CTG-CAG-AGG-CAG-TTG-G-3'). Primer extension analysis was performed by the method of Jones et al., Cell 48: 79-89 (1987), using the synthetic oligonucleotide wherein the 5' terminus was labeled with [$^{32}$P]. No band was found in the reaction with RNA isolated from control cells, whereas two bands were detected in the reaction with RNA isolated from elicitor-treated cells. The major product was 186 nucleotides in length and corresponded to the position of the first 'A' in the sequence (SEQ ID NO: 5) CCCTCAATCT, which closely resembles an eukaryotic transcription initiator sequence [Smale and Baltimore, Cell 57:103–113 (1989)]. This position was designated as +1. An additional product two nucleotides smaller than the major reverse transcript was also detected. The putative translational initiation codon was 55 bp downstream from the major transcription start site.

EXAMPLE X

Flanking Sequences

Putative TATA and CAAT boxes were located 44 and 75 bp respectively upstream from the transcription start site (see Sequence ID No. 1) The DNA sequence between these two boxes was GC-rich (72%). Two inverted putative GC boxes were present at positions −55 to −60 and −66 to −70 [Kadonaga et al., Trends Biochem. Sci. 11:20–23 (1986)]. A sequence similar to the binding site for an elicitor-inducible factor in a parsley phenylalanine ammonia-lyase promoter occurred in the inverted orientation at positions −108 to −117 [Lois et al., EMBO J. 8: 1641–1648 (1989)]. An imperfectly duplicated TGTCCACGT motif was located at positions −752 to −736. In vivo footprinting studies have demonstrated constitutive binding of a nuclear factor to this motif [Lois et al., supra). Putative cis-acting elements in the 5' flanking region of RCH10 are summarized in Table 1:

TABLE 1

Repeat sequences and putative cis-elements in the RCH10 promoter

| Class | Position* | Sequence |
|---|---|---|
| TATA box | 1836–1843 | TATATAA |
| CAT box | 1806–1810 | CCAAT |
| GC box-like motif | 1815–1819 | CGCCC(inverted) |
| | 1824–1830 | CCCGCGG(inverted) |
| Elicitor-inducible PAL** footprint | 1770–1778 | TGGCAATGC(inverted) |
| Constitutive | 1133–1139 | TGTCCAA |
| PAL footprint | 1140–1146 | TGTCCAC |
| Direct repeat 1 | 331–343 | GTATGTAAAAAG (SEQ ID NO: 18) |
| | 363–374 | GTATGTAAAAAG (SEQ ID NO: 18) |
| Direct repeat 2 | 748–759 | TGGGAGCAGCGG (SEQ ID NO: 19) |
| | 912–923 | TGGGAGCAGCGG (SEQ ID NO: 19) |
| Direct repeat 3 | 1459–1473 | TACTCTGTGTGATGA (SEQ ID NO: 20) |
| | 1494–1507 | TACT—TGTGTGATGA (SEQ ID NO: 21) |
| Inverted repeat 1 | 541–550 | AATTTTTTAA (SEQ ID NO: 22) |
| | 1229–1238 | TTAAAAAATT (SEQ ID NO: 23) |
| Inverted repeat 2 | 1257–1266 | TCCCCAAGGT (SEQ ID NO: 24) |
| | 1650–1659 | TGGAACCCCT (SEQ ID NO: 25) |
| Triplicated motif | 1723–1738 | A<u>TGCATGCAT</u>AT<u>GCAT</u> (SEQ ID NO: 26) |

*Numbers refer to the sequence presented in Sequence ID No 1
**PAL = phenylalanine ammonia-lyase A computer-aided search failed to identify significant sequence homology between the rice RCH10 promoter and the promoter of an ethylene-inducible bean chitinase [Broglie et al., Proc. Natl. Acad. Sci. USA 83:6820–6824 (1989)]. Two putative polyadenylation signals at positions 1054 (AAATAA; see Sequence ID No. 2) and 1093 (AATAAA; see Sequence ID No. 2) were found in the 3' flanking region. These sequences fit the consensus polyadenylation sequence (A/GAATAA) described in plants [Heidecker and Messing, Annu. Rev. Plant Physiol. 37:439–466 (1986)].

EXAMPLE XI

Organization of Rice Chitinase Genes

To estimate the number of chitinase genes in the rice genome, Southern blots of genomic DNA from rice were hybridized with the SacII-HindIII fragment of pRCH10 (positions 422 to 1021; see Sequence ID No. 2), which encodes a region conserved among class I and class II chitinases. This probe hybridized to several restriction fragments of rice genomic DNA digested with EcoRI, ClaI, HindIII or PvuII, indicating the presence of a family of chitinase genes in the rice genome.

EXAMPLE XII

Chitinase Gene Expression in Plants and Elicitor-treated Cell Populations

RNA isolated from rice cell suspension cultures treated with the Pmg fungal elicitor were hybridized with the fragment from the conserved region of the RCH10 gene, and also with an RCH10-specific sequence, the SphI-MluI fragment (positions 114 to 259; see Sequence ID No. 2). A low basal level of chitinase transcripts could be detected in cells of suspension cultures when the fragment from the conserved region was used as probe. However, when the RCH10-specific fragment was used as the probe, no basal level of transcripts was detectable. Thus, the basal level of chitinase transcripts in cells in cultured suspension was not due to RCH10, but represented the expression of other members of the gene family. Following treatment with Pmg elicitor, accumulation of chitinase transcripts could be detected within 2 hours, with maximum levels after 6 hours. Hybridization with the RCH10-specific probe showed a similar marked accumulation of the RCH10 transcript over the time course of 2–6 hours. Northern blot analysis of RNA from different organs showed that transcripts of rice chitinase accumulate to high levels in roots, but only to barely detectable levels in stems and leaves.

EXAMPLE XIII

Construction of Gene Fusions

A 2538 bp HindIII fragment from the RCH10 gene was subcloned into pGEM7, and a HindIII/BalI fragment (a contiguous fragment containing nucleotides 372–1884 of Sequence ID No. 1, plus nucleotides 1–76 of Sequence ID No. 2) was then inserted into the HindIII/SmaI site of the GUS expression vector pBI101.2 [Jefferson et al., EMBO J 6: 3901–3907 (1987)] to give pBZ4. A 1463 bp HincII fragment from RCH10 was cloned into the pGEM7 SmaI site, and a XbaI/BalI fragment (a contiguous fragment containing nucleotides 1558–1884 of Sequence ID No. 1, plus nucleotides 1–76 of Sequence ID No. 2) was then inserted into the XbaI/SmaI site of pBI101.2 to give pBZ14. A 276 bp SphI fragment from RCH10 was cloned into pSP72, and a HindIII/BalI fragment (a contiguous fragment containing nucleotides 1724–1884 of Sequence ID No. 1, plus nucleotides 1–76 of Sequence ID No. 2) was then inserted into the HindIII/SmaI site of pBI101.2 to give pBZ10. The RCH10-GUS translational fusions in pBZ4, pBZ14 and pBZ10 were confirmed by direct double-stranded sequencing using a GUS-specific primer.

EXAMPLE XIV

Tobacco Transformation pBZ4, pBZ14 and pBZ10 were mobilized from Escherichia coli HB101 into Agrobacterium tumefaciens LBA 4404 [Jefferson et al., supra], and transgenic tobacco plants generated by the leaf disc method [Rogers et al., Methods Enzym. 118:627–640 (1986)]. Transformed plants were selected on Murashige and Skoog medium [Murashige and Skoog, supra] containing 200 µg/ml kanamycin and 500 µg/ml carbenicillin or cefatoxim, and grown at 25° C. under a 16-hour light (115 mE)/8-hour dark cycle.

EXAMPLE XV

Wound and Elicitor Induction

Discs (about 8 mm in diameter) excised from fully expanded leaves were incubated in 50 mM sodium phosphate buffer (pH 7.0) at 25° C. in the dark. Tissue samples were snap frozen in liquid nitrogen and stored at −80° C. Fungal elicitor was the high molecular weight fraction heat-released from washed mycelial walls of Phytophthora megasperma f.sp. glycinea [Ayers et al., Plant Physiol. 57: 760–765 (1976)], and was applied to wounded tissue in 50 mM sodium phosphate buffer (pH 7.0) at a final concentration of 100 µg glucose equivalents/ml.

Excision wounding of leaf tissue caused a marked increase in GUS activity. In transformants BZ4-1 and BZ4-14, wounding resulted in 10- to 20-fold increases in GUS activity (relative to the low basal levels of 49 and 22 pmole of product/minute/mg protein, respectively, in unwounded tissue; see FIG. 3A). In transformants BZ4-5 and BZ4-7, the levels of GUS activity in unwounded leaves were 920 and 570 pmole/minute/mg protein, and wounding caused a 2- to 3-fold increase in these relatively high basal levels.

Figure 4A:
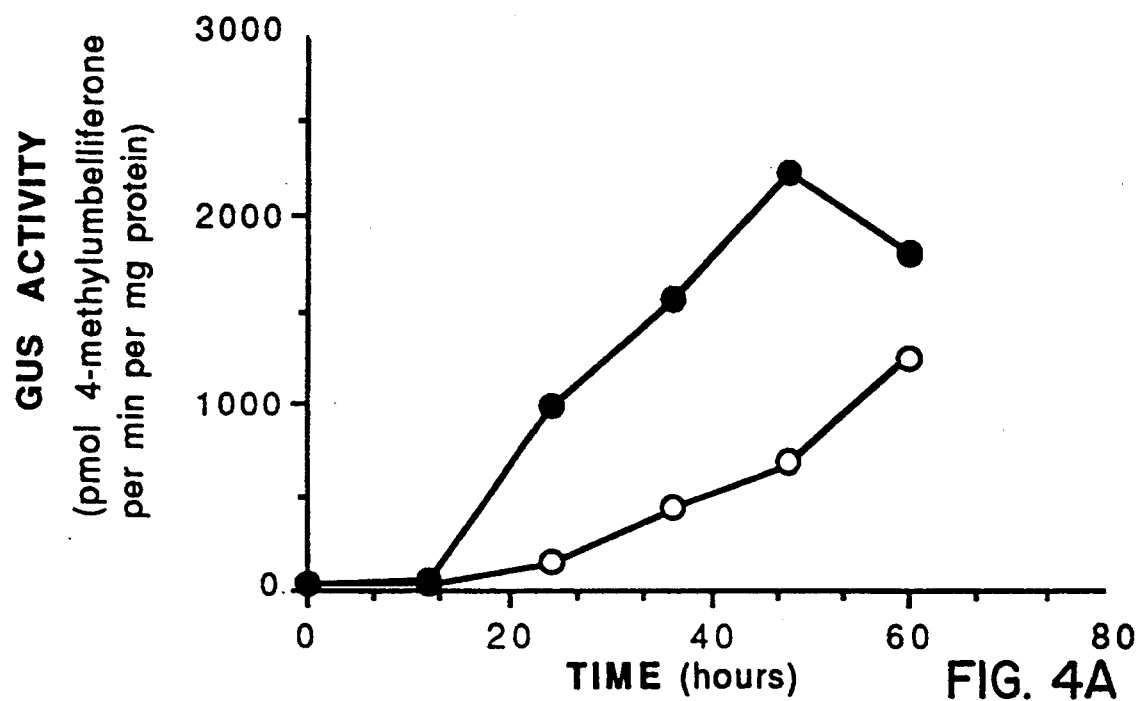
FIG. 4A presents results using a substantially intact promoter (including nucleotides −1512 to +76, with respect to the transcription start site; also presented as nucleotides 374–1884 of Sequence ID No. 1, plus nucleotides 1–76 of Sequence ID No. 2; referred to as construct BZ4-1)
Figure 4B:
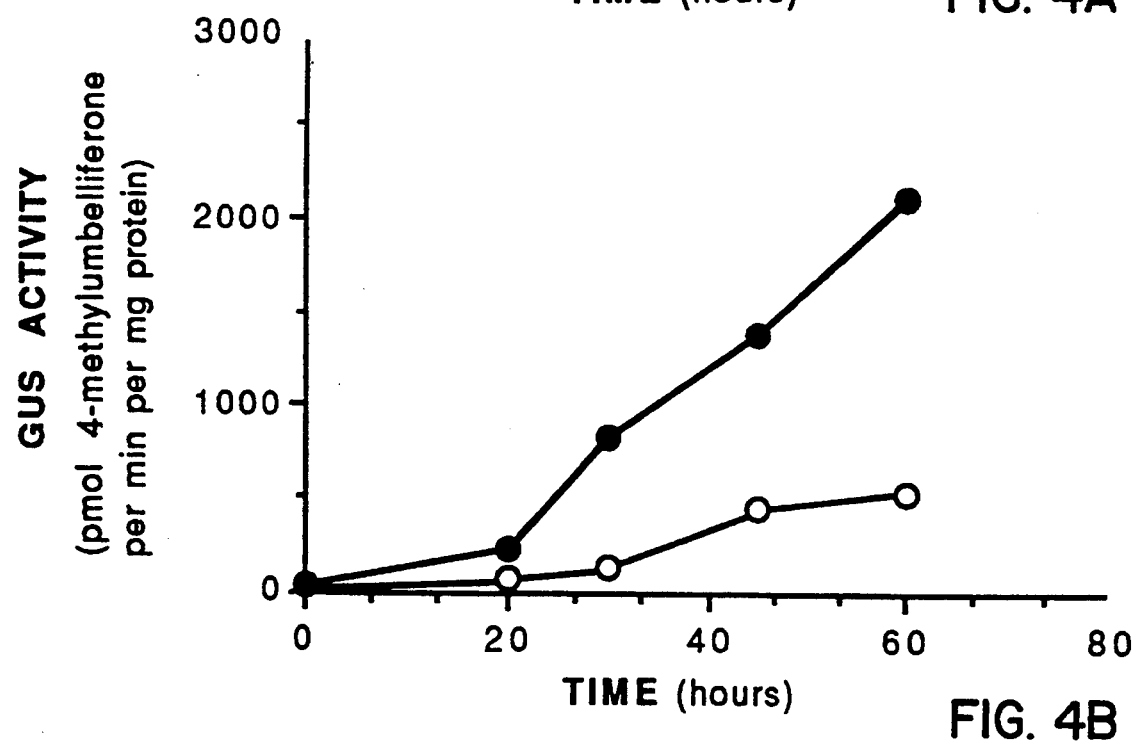
FIG. 4B presents results with a deleted promoter (including only nucleotides −160 to +76, with respect to the transcription start site; also presented as nucleotides 1724–1884 of Sequence ID No. 1, plus nucleotides 1–76 of Sequence ID No. 2; referred to as construct BZ10-1). Open circles designate wounded leaves, while closed circles designate wounded leaves which have also been exposed to elicitor.

Addition of fungal elicitor to the leaf tissue immediately after excision caused a further marked stimulation of the expression of the gene fusion, compared with equivalent excision-wounded tissue not treated with elicitor (see FIG. 4A). Increased GUS activity was observed 16 hours after elicitor treatment with maximum levels after 48 hours (see FIG. 4A), whereas the response to excision wounding in the absence of elicitor was somewhat slower. Overall, elicitor treatment of excised leaf discs caused a 40- to 60-fold increase in GUS activity over low basal levels in BZ4-1 and BZ4-14 plants, compared with a 4- to 6-fold increase in BZ4-5 and BZ4-7 plants, which exhibited higher basal levels of expression (see FIG. 3A).

Histochemical analysis of GUS activity in situ showed that wound induction of the gene fusion was restricted to the tissues immediately adjacent to the wound surface, whereas elicitor also induced expression in tissues at a somewhat greater distance from the wound surface. Ethylene, administered as ethephon, had no effect on the level of GUS activity in intact leaves.

EXAMPLE XVI

Developmental Expression

Figure 3B:
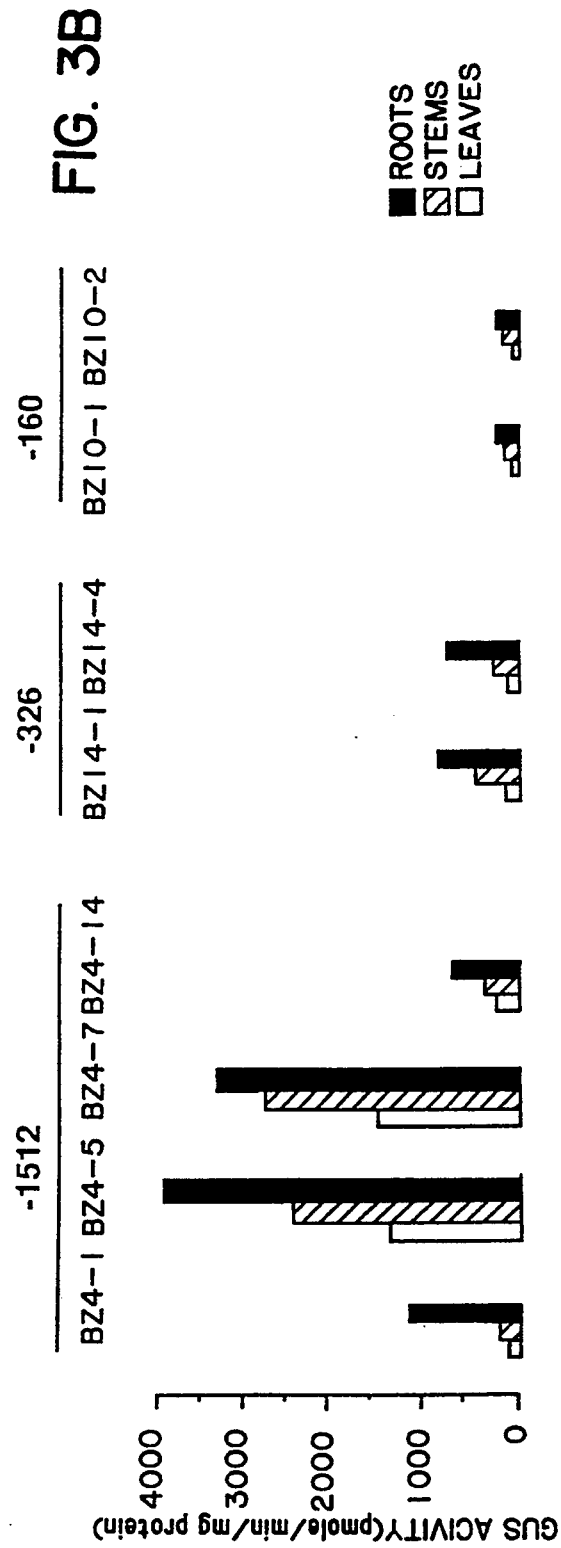
FIG. 3B deals with developmental expression in vegetative organs.

In addition to elicitor and wound induction in leaf tissue, the RCH10-GUS gene fusion was also expressed during normal development in the absence of an applied stress. Thus, high levels of GUS were observed in roots and moderate levels in stems compared to the relatively weak expression in young leaves (see FIG. 3B). Although there was, as expected, some variation among the independent transformants in the absolute levels of expression, the same overall pattern of GUS activity was observed in each case: root>stem>leaf. Histochemical analysis showed strong expression of RCH10-GUS in juvenile tissue of apical root tips. In stems, GUS staining was localized to the epidermis and vascular system. In the latter, staining was not restricted to specific tissue-types, but was observed in a number of locations including the outer phloem, inner phloem and xylem. No GUS staining was observed in pith or cortical tissue.

Figure 3C:
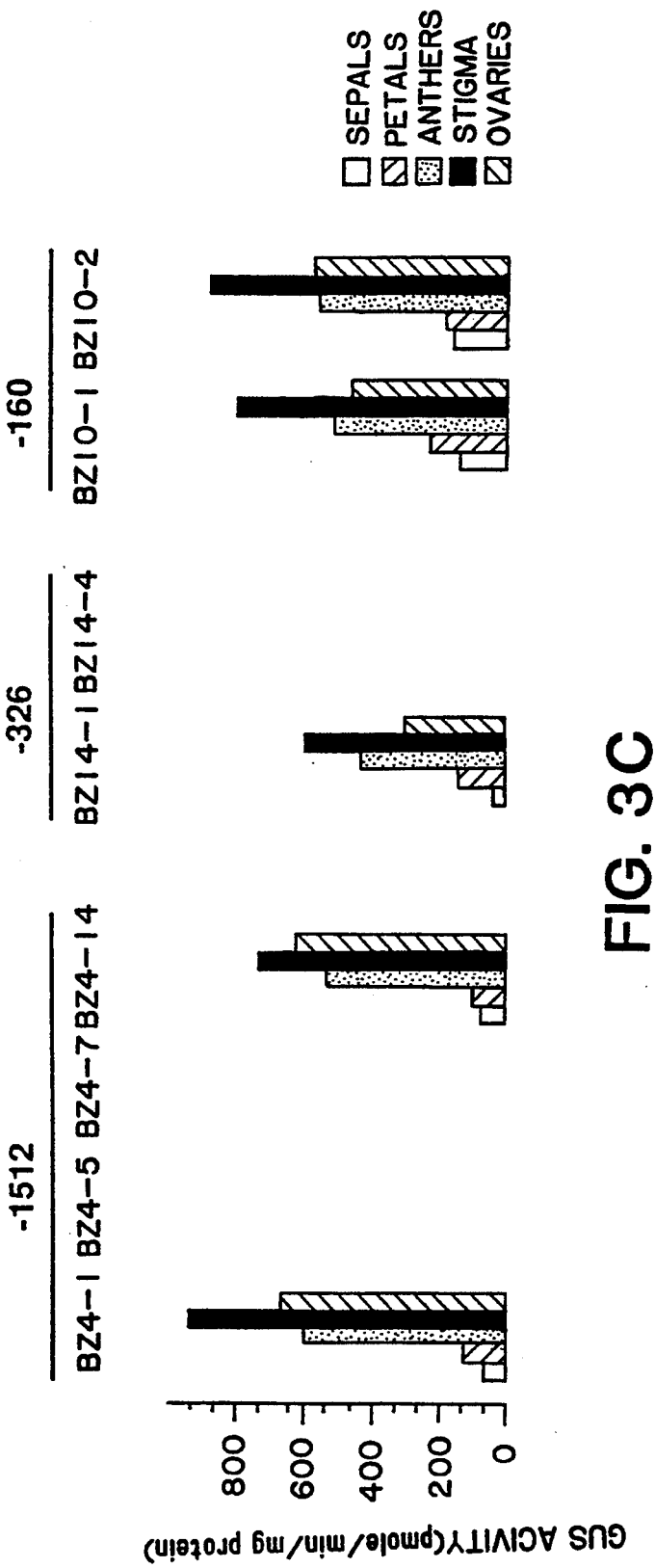
FIG. 3C deals with developmental expression in floral organs.

The RCH10-GUS gene fusion also exhibited a characteristic pattern of expression in floral organs. Thus while only low levels of GUS activity were observed in sepals and petals, comparable to the levels in leaves from the same plants, relatively high levels were found in anther, stigma and ovary extracts (see FIG. 3C). This organ-specific pattern of expression was confirmed by histochemical analysis of GUS activity in situ. Moreover, the in situ analysis showed that within anthers there was strong expression of the gene fusion specifically in pollen, since no staining was observed with ruptured anthers from which the pollen had been expelled, whereas strong staining was readily detectable with intact anthers containing mature pollen. GUS activity was also directly demonstrated by histochemical staining of isolated pollen.

EXAMPLE XVII

Promoter Deletions

To localize cis-elements that specify the complex developmental regulation and stress induction of the RCH10 promoter, the expression was analyzed for gene fusions with upstream (i.e., 5') portions of the promoter deleted, e.g., deleted to position 1558 (see Sequence ID No. 1; BZ14) and deleted to position 1724 (see Sequence ID No. BZ10). Ten independent BZ14 transformants and 7 BZ10 transformants were examined, and in both cases two representative plants were analyzed in further detail. Strikingly, the full pattern of expression established for the BZ4 plants containing the promoter to deleted only to nucleotide 372 (see Sequence ID No. 1) was also observed in plants containing the much more extensive deletions, i.e., BZ14 (deleted to position 1558, refer to Sequence ID No. 1) or BZ10 (deleted to position 1724, refer to Sequence ID No. 1) See FIG. 3B. Thus, the BZ14 and BZ10 transformants exhibited wounding and elicitor induction of GUS activity from low basal levels in leaf tissue, with similar fold-inductions over basal levels and similar absolute levels of GUS activity in induced tissue as observed in BZ4 plants containing the full promoter (containing nucleotides 372 to 1884 as presented in Sequence ID No. 1). Likewise, the kinetics for wounding and elicitor induction of the constructs containing substantial promoter deletions (i.e., the 1558-1884 and 1724-1884 constructs) were the same as with the full promoter. The BZ14 and BZ10 plants also showed the same characteristic pattern of expression in floral organs as observed with the full promoter, with high levels of GUS activity in anthers, stigmas and ovaries compared to relatively weak expression in sepals and petals (see FIG. 3C). In vegetative organs of BZ14 and BZ10 transformants, the levels of GUS activity were: root>stem>leaf, as observed with the full promoter, although the expression in roots and stems was markedly reduced compared to BZ4 plants (see FIG. 3B).

EXAMPLE XVIII

GUS Assays

GUS activity was assayed in tissue extracts by fluorimetric determination of the production of 4-methylumbelliferone from the corresponding $\beta$-glucuronide [Jefferson et al. supra; Jefferson, Plant Mol. Biol. Rep. 5: 387–405 (1987)]. Root, stem and leaf tissues were collected from 10 cm-tall plantlets and floral organs were collected from mature fully open flowers. Protein was determined by the method of Bradford [Anal. Biochem. 72: 248–254 (1976) and GUS activity was expressed as pmole of product/minute/mg of protein. Histochemical localization of GUS activity in situ was performed with the chromogenic substrate 5-bromo-4-chloro-3-indolyl $\beta$-D-glucuronide (X-gluc). Stem sections were cut by hand, vacuum-infiltrated with 50 mM sodium phosphate buffer (pH 7.0) containing X-gluc and incubated at 37° C. Flowers and roots were directly incubated in X-gluc solution. After overnight incubation, chlorophyll was removed by immersion of the tissue samples in 70% ethanol prior to examination using a Nikon Diaphot TMD microscope.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the nucleic acid sequence for a regulatory region (i.e., the upstream or 5'region) of a rice chitinase gene of the invention.

Sequence ID No. 2 is the nucleic acid sequence and deduced amino acid sequence for a rice chitinase gene according to the present invention.

Sequence ID No. 3 is the deduced amino acid sequence for the rice chitinase gene presented in Sequence ID No. 2.

Sequence ID No. 4 is the nucleic acid sequence of a 28-mer oligonucleotide used in primer-extension analysis to identify the transcription start site.

Sequence ID No. 5 is a partial nucleic acid sequence of the transcription start site.

Sequence ID No. 6 is the predicted amino acid sequence of tobacco basic chitinase.

Sequence ID Nos. 7–8 are predicted amino acid sequences of potato basic chitinases.

Sequence ID No. 9 is the predicted amino acid sequence of bean basic chitinase.

Sequence ID No. 10 is the amino acid sequence of rubber hevein domain.

Sequence ID Nos. 11–12 are the amino acid sequences of potato WIN1 and WIN2 hevein domains, respectively.

Sequence ID No. 13 is the amino acid sequence of wheat germ agglutinin isolectin, WGA, hevein domain.

Sequence ID No. 14 is the amino acid sequence of bean basic chitinase hevein domain.

Sequence ID No. 15 is the amino acid sequence of tobacco basic chitinase hevein domain.

Sequence ID No. 16 is the amino acid sequence of tobacco PR-Q hevein domain.

Sequence ID No. 17 is the amino acid sequence of tobacco PR-P hevein domain.

Sequence ID Nos. 18–21 are nucleic acid sequences of direct repeat sequences in the RCH10 promoter.

Sequence ID Nos. 22–25 are nucleic acid sequences of inverted repeat sequences in the RCH10 promoter.

Sequence ID No. 26 is the nucleic acid sequence of a triplicated sequence motif in the RCH10 promoter.

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 1884 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
GTTAACTGCC AGCTTCAAAT TATTTATAGA TAATTTAATA GCCAATTCAT CTAATAGTTA      60
TTTATTATAC TATTAATATC TGATCTCACC TGAGTCATAC TACAGCTGGC TACAAATGTG     120
TAGTGTACTA CTCTTTCTCT CTTCTTTTAT CTCTTTAAAA TATGTTATAG CGGCTTATAA     180
CTGTTATTGT ACCTGCTCTA AGTCGATCGT GATGATCGAT CATTCGTCAA ATGTTACCAC     240
GTCCAGTGAC TTATCCATGG TTCACCTTAC TATAAAAAAT GATTTTTATG GACAACTCCT     300
TTAATTTGT  TCAAACGGAC CAAAGAAACC CGTATGTAAA AAGGTTGGGA ATATCTGATC     360
CTGTATGTAA AAAGCTTGGA ATATCTGATA GAGGGCAAAC TTGTGAAAAT TGTTTTTTTA     420
AGATGGACCT CTTAACAAGC CTACTTGCAA AAAATCGACC TATTTACATA GACGGACTTG     480
TTAAGAGACT TGTCTATGAA AATCGGTGGA TAGCATGACC GGTCACAATA CTTCCCCTAT     540
AATTTTTTAA TCCTCCTAGA TAAACCCTAT CTCTCTCTTC ATGTTCTTTG CTTTCCATCT     600
ATAGTCTCGC ATCCCTCATC ACCTCCATT  CCTCTCTCTC TCACCCCCTG CTCAGTGGGA     660
GCGCAGCTGG CGATGGCACC ACCGGCGACA AGAGGGGCCA GAGGCTAGCA TGTGCACGGA     720
AGTGACAATG GCGCCACATG ATTAGCATGG GAGCAGCGGC GCGTTTCATC AGGACACGCT     780
GCAATTGGCT CTAGTGACGG CACCCTTGAG AGGACATGGT AGCGGTGGCG CCTCAGGAGT     840
GGTGGGGCAC GGTGGCAGAA CTCCGGCGGT GGCAAGCCAC CACACAGCGA CAGATCCACC     900
ACCACCGACC TTGGGAGCAG CGGGGCCTCA GCGGTGATGA CGATGGTAGA TCGAAGCTAG     960
GGTTTCTATT TTTTTTGCT  GCAAAAATCA CTTTTTACAC ATGGGTACAT GCATGTTTTT    1020
TACATACACC TAGTATTAGG TGGGCCGTCC ACCCGTTCGC AAAGATCATT TATGCAGTCA    1080
TCATGATCGG AGATGGAACT ATGGAGACAT ATATGCAAGT ATTTGGCCAA CATGTCCAAT    1140
GTCCACCAGA TTGGGAGCTC AATCCTACCC CGTGGTATGG GTATGTTACT GTGCGCCTAA    1200
TATTTACGTA CGCTGGTTTA ATCTATTTTT AAAAAATTTG CTACATACTC CCTCCGTCCC    1260
CAAGGTTGGC TTTTTTTTTT TGGAGGGAGA GAGTAATATT TAGAGTTTGT GGTTTTGTT     1320
ATTGAACACC TTAAAAGGCA TGAAACGACT TGTCGGAGAA CGAATCTCCT CTAGCAGGGA    1380
AGCAACGAAC CTCCCAAAAA AAACAAAAAA AAACTCCTCC TTTCATGATT CAACCAAAGG    1440
GCAATTTGAG ATCGAGCCTA CTCTGTGTGA TGAACTCAAA ACACAATCAA GTATACTTGT    1500
GTGATGAGCG GTGAGCCAGA TATGTTCCTG CTCTGTCCGT GCTCGACTCA ATTCATTGTC    1560
```

| | | |
|---|---|---|
| AACCCTAGCG ATTTCCATTA ATGCAATGAC TATATGAAAT GCAAAGATGT ACTATATGAC | | 1620 |
| TACTAGTTGG ATGCACAATA GTGCTACTAT GGAACCCCTT TTGCCCCTCT AATAGTAGGA | | 1680 |
| TCTAGGCTAA ATGACGTTTC AATAAATCAC AGTTAGTAAG GGATGCATGC ATATGCATGA | | 1740 |
| TATGTGAGTG TCTGTTAATC GTGGCAAATT GGCAATGCAA TTTGTTGTTG AAAATACCA | | 1800 |
| AGATGCCAAT ACTACGCCCA CTTCCGCGG CGCTCTATAT AAAGCCATGC GCTCCCATCG | | 1860 |
| CTTCTTCCTC ACAAACTTTC CCTC | | 1884 |

( 2 ) INFORMATION FOR SEQ ID NO:2:

( i ) SEQUENCE CHARACTERISTICS:
        ( A ) LENGTH: 1151 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 55..1062

( x i ) SEQUENCE DESCRIPTION: SEQ ID NO:2:

```
AATCAGTCAA TCTGTATACA GCAACTCAGC GATCTTATAT TTACCCAACA CACC ATG          57
                                                             Met
                                                              1

AGA GCG CTC GCT GTG GTG GCC ATG GTG GCC AGG CCC TTC CTC GCG GCG         105
Arg Ala Leu Ala Val Val Ala Met Val Ala Arg Pro Phe Leu Ala Ala
         5                  10                  15

GCC GTG CAT GCC GAG CAG TGC GGC AGC CAG GCC GGC GGC GCG GTG TGC         153
Ala Val His Ala Glu Gln Cys Gly Ser Gln Ala Gly Gly Ala Val Cys
             20                  25                  30

CCC AAC TGC CTC TGC TGC AGC CAG TTC GGC TGG TGC GGC TCC ACC TCC         201
Pro Asn Cys Leu Cys Cys Ser Gln Phe Gly Trp Cys Gly Ser Thr Ser
     35                  40                  45

GAC TAC TGC GGC GCC GGA TGC CAG AGC CAG TGC TCG CGG CTG CGG CGG         249
Asp Tyr Cys Gly Ala Gly Cys Gln Ser Gln Cys Ser Arg Leu Arg Arg
 50                  55                  60                  65

CGG CGG CCC GAC GCG TCC GGC GGC GGT GGC AGC GGC GTC GCG TCC ATC         297
Arg Arg Pro Asp Ala Ser Gly Gly Gly Gly Ser Gly Val Ala Ser Ile
                 70                  75                  80

GTG TCG CGC TCG CTC TTC GAC CTG ATG CTG CTC CAC CGC AAC GAT GCG         345
Val Ser Arg Ser Leu Phe Asp Leu Met Leu Leu His Arg Asn Asp Ala
             85                  90                  95

GCG TGC CCG GCC AGC AAC TTC TAC ACC TAC GAC GCC TTC GTC GCC GCC         393
Ala Cys Pro Ala Ser Asn Phe Tyr Thr Tyr Asp Ala Phe Val Ala Ala
        100                 105                 110

GCC AGC GCC TTC CCG GGC TTC GCC GCC GCG GGC GAC GCC GAC ACC AAC         441
Ala Ser Ala Phe Pro Gly Phe Ala Ala Ala Gly Asp Ala Asp Thr Asn
    115                 120                 125

AAG CGC GAG GTC GCC GCG TTC CTT GCG CAG ACG TCC CAC GAG ACC ACC         489
Lys Arg Glu Val Ala Ala Phe Leu Ala Gln Thr Ser His Glu Thr Thr
130                 135                 140                 145

GGC GGG TGG GCG ACG GCG CCC GAC GGC CCC TAC ACG TGG GGC TAC TGC         537
Gly Gly Trp Ala Thr Ala Pro Asp Gly Pro Tyr Thr Trp Gly Tyr Cys
                150                 155                 160

TTC AAG GAG GAG AAC GGC GGC GCC GGG CCG GAC TAC TGC CAG CAG AGC         585
Phe Lys Glu Glu Asn Gly Gly Ala Gly Pro Asp Tyr Cys Gln Gln Ser
            165                 170                 175

GCG CAG TGG CCG TGC GCC GCC GGC AAG AAG TAC TAC GGC CGG GGT CCC         633
Ala Gln Trp Pro Cys Ala Ala Gly Lys Lys Tyr Tyr Gly Arg Gly Pro
        180                 185                 190

ATC CAG CTC TCC TAC AAC TTC AAC TAC GGG CCG GCG GGG CAG GCC ATC         681
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Ile | Gln | Leu | Ser | Tyr | Asn | Phe | Asn | Tyr | Gly | Pro | Ala | Gly | Gln | Ala | Ile |      |
|     | 195 |     |     |     | 200 |     |     |     |     | 205 |     |     |     |     |     |      |
| GGC | GCC | GAC | CTG | CTC | GGC | GAC | CCG | GAC | CTC | GTG | GCG | TCT | GAC | GCC | ACC | 729  |
| Gly | Ala | Asp | Leu | Leu | Gly | Asp | Pro | Asp | Leu | Val | Ala | Ser | Asp | Ala | Thr |      |
| 210 |     |     |     |     | 215 |     |     |     |     | 220 |     |     |     |     | 225 |      |
| GTC | TCC | TTC | GAC | ACG | GCC | TTC | TGG | TTC | TGG | ATG | ACG | CCG | CAG | TCG | CCC | 777  |
| Val | Ser | Phe | Asp | Thr | Ala | Phe | Trp | Phe | Trp | Met | Thr | Pro | Gln | Ser | Pro |      |
|     |     |     |     | 230 |     |     |     |     | 235 |     |     |     |     | 240 |     |      |
| AAG | CCG | TCG | TGC | AAC | GCG | GTC | GCC | ACC | GGC | CAG | TGG | ACG | CCC | TCC | GCC | 825  |
| Lys | Pro | Ser | Cys | Asn | Ala | Val | Ala | Thr | Gly | Gln | Trp | Thr | Pro | Ser | Ala |      |
|     |     |     | 245 |     |     |     |     | 250 |     |     |     |     | 255 |     |     |      |
| GAC | GAC | CAG | CGG | GCG | GGC | CGC | GTG | CCG | GGC | TAC | GGC | GTC | ATC | ACC | AAC | 873  |
| Asp | Asp | Gln | Arg | Ala | Gly | Arg | Val | Pro | Gly | Tyr | Gly | Val | Ile | Thr | Asn |      |
|     |     |     | 260 |     |     |     |     | 265 |     |     |     |     | 270 |     |     |      |
| ATC | ATC | AAC | GGC | GGG | CTG | GAG | TGC | GGC | CAT | GGC | GAG | GAC | GAT | CGC | ATC | 921  |
| Ile | Ile | Asn | Gly | Gly | Leu | Glu | Cys | Gly | His | Gly | Glu | Asp | Asp | Arg | Ile |      |
| 275 |     |     |     |     | 280 |     |     |     |     | 285 |     |     |     |     |     |      |
| GCC | GAC | CGG | ATC | GGC | TTC | TAC | AAG | CGC | TAC | TGC | GAC | ATC | CTC | GGC | GTC | 969  |
| Ala | Asp | Arg | Ile | Gly | Phe | Tyr | Lys | Arg | Tyr | Cys | Asp | Ile | Leu | Gly | Val |      |
| 290 |     |     |     |     | 295 |     |     |     |     | 300 |     |     |     |     | 305 |      |
| AGC | TAC | GGC | GCC | AAC | TTG | GAT | TGC | TAC | AGC | CAG | AGG | CCT | TCG | GCT | CCT | 1017 |
| Ser | Tyr | Gly | Ala | Asn | Leu | Asp | Cys | Tyr | Ser | Gln | Arg | Pro | Ser | Ala | Pro |      |
|     |     |     |     | 310 |     |     |     |     | 315 |     |     |     |     | 320 |     |      |
| CCT | AAG | CTT | CGC | CTA | CCT | AGC | TTC | CAC | ACA | GTG | ATA | AAT | AAT | CAC |     | 1062 |
| Pro | Lys | Leu | Arg | Leu | Pro | Ser | Phe | His | Thr | Val | Ile | Asn | Asn | His |     |      |
|     |     |     | 325 |     |     |     |     | 330 |     |     |     |     | 335 |     |     |      |

TGATGGAGTA TAGTTTACAC CATATCGATG AATAAAACTT GATCCGAATT CTCGCCCTAT 1122

AGTGAGTCGT ATTAGTCGAC AGCTCTAGA 1151

( 2 ) INFORMATION FOR SEQ ID NO:3:

( i ) SEQUENCE CHARACTERISTICS:
        ( A ) LENGTH: 336 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

|     |     |     |     |     |     |     |     |     |     |     |     |     |     |     |
| --- | --- | --- | --- | --- | --- | --- | --- | --- | --- | --- | --- | --- | --- | --- |
| Met | Arg | Ala | Leu | Ala | Val | Val | Ala | Met | Val | Ala | Arg | Pro | Phe | Leu | Ala |
| 1   |     |     |     | 5   |     |     |     |     | 10  |     |     |     |     | 15  |     |
| Ala | Ala | Val | His | Ala | Glu | Gln | Cys | Gly | Ser | Gln | Ala | Gly | Gly | Ala | Val |
|     |     |     |     | 20  |     |     |     | 25  |     |     |     |     | 30  |     |     |
| Cys | Pro | Asn | Cys | Leu | Cys | Cys | Ser | Gln | Phe | Gly | Trp | Cys | Gly | Ser | Thr |
|     |     |     | 35  |     |     |     |     | 40  |     |     |     |     | 45  |     |     |
| Ser | Asp | Tyr | Cys | Gly | Ala | Gly | Cys | Gln | Ser | Gln | Cys | Ser | Arg | Leu | Arg |
|     | 50  |     |     |     |     | 55  |     |     |     |     | 60  |     |     |     |     |
| Arg | Arg | Arg | Pro | Asp | Ala | Ser | Gly | Gly | Gly | Gly | Ser | Gly | Val | Ala | Ser |
| 65  |     |     |     |     | 70  |     |     |     |     | 75  |     |     |     |     | 80  |
| Ile | Val | Ser | Arg | Ser | Leu | Phe | Asp | Leu | Met | Leu | Leu | His | Arg | Asn | Asp |
|     |     |     |     | 85  |     |     |     |     | 90  |     |     |     |     | 95  |     |
| Ala | Ala | Cys | Pro | Ala | Ser | Asn | Phe | Tyr | Thr | Tyr | Asp | Ala | Phe | Val | Ala |
|     |     |     | 100 |     |     |     |     | 105 |     |     |     |     | 110 |     |     |
| Ala | Ala | Ser | Ala | Phe | Pro | Gly | Phe | Ala | Ala | Ala | Gly | Asp | Ala | Asp | Thr |
|     |     |     | 115 |     |     |     |     | 120 |     |     |     |     | 125 |     |     |
| Asn | Lys | Arg | Glu | Val | Ala | Ala | Phe | Leu | Ala | Gln | Thr | Ser | His | Glu | Thr |
|     | 130 |     |     |     |     | 135 |     |     |     |     | 140 |     |     |     |     |
| Thr | Gly | Gly | Trp | Ala | Thr | Ala | Pro | Asp | Gly | Pro | Tyr | Thr | Trp | Gly | Tyr |
| 145 |     |     |     |     | 150 |     |     |     |     | 155 |     |     |     |     | 160 |
| Cys | Phe | Lys | Glu | Glu | Asn | Gly | Gly | Ala | Gly | Pro | Asp | Tyr | Cys | Gln | Gln |

|   | 165 | 170 | 175 |
|---|---|---|---|

Ser Ala Gln Trp Pro Cys Ala Ala Gly Lys Lys Tyr Tyr Gly Arg Gly
            180                 185                 190

Pro Ile Gln Leu Ser Tyr Asn Phe Asn Tyr Gly Pro Ala Gly Gln Ala
            195                 200                 205

Ile Gly Ala Asp Leu Leu Gly Asp Pro Asp Leu Val Ala Ser Asp Ala
    210                 215                 220

Thr Val Ser Phe Asp Thr Ala Phe Trp Phe Trp Met Thr Pro Gln Ser
225                 230                 235                 240

Pro Lys Pro Ser Cys Asn Ala Val Ala Thr Gly Gln Trp Thr Pro Ser
                245                 250                 255

Ala Asp Asp Gln Arg Ala Gly Arg Val Pro Gly Tyr Gly Val Ile Thr
            260                 265                 270

Asn Ile Ile Asn Gly Gly Leu Glu Cys Gly His Gly Glu Asp Asp Arg
    275                 280                 285

Ile Ala Asp Arg Ile Gly Phe Tyr Lys Arg Tyr Cys Asp Ile Leu Gly
    290                 295                 300

Val Ser Tyr Gly Ala Asn Leu Asp Cys Tyr Ser Gln Arg Pro Ser Ala
305                 310                 315                 320

Pro Pro Lys Leu Arg Leu Pro Ser Phe His Thr Val Ile Asn Asn His
                325                 330                 335

( 2 ) INFORMATION FOR SEQ ID NO:4:

( i ) SEQUENCE CHARACTERISTICS:
      ( A ) LENGTH: 25 base pairs
      ( B ) TYPE: nucleic acid
      ( C ) STRANDEDNESS: unknown
      ( D ) TOPOLOGY: unknown ( i i ) MOLECULE TYPE: DNA (genomic)

( x i ) SEQUENCE DESCRIPTION: SEQ ID NO:4:

CCGAACTGGC TGCAGAGGCA GTTGG                                    25

( 2 ) INFORMATION FOR SEQ ID NO:5:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:5:

CCCTCAATCT                                                     10

( 2 ) INFORMATION FOR SEQ ID NO:6:

( i ) SEQUENCE CHARACTERISTICS:
      ( A ) LENGTH: 310 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:6:

Met Ser Leu Leu Leu Leu Ser Ala Ser Ala Glu Gln Cys Gly Ser Gln
1               5                   10                  15

Ala Gly Gly Ala Arg Cys Ala Ser Gly Leu Cys Cys Ser Lys Phe Gly
            20                  25                  30

Trp Cys Gly Asn Thr Asn Asp Tyr Cys Gly Pro Gly Asn Cys Gln Ser

```
                          35                          40                          45

Gln  Cys  Pro  Gly  Gly  Pro  Thr  Pro  Pro  Gly  Gly  Gly  Asp  Leu  Gly  Ser
                  50                      55                      60

Ile  Ile  Ser  Ser  Ser  Met  Phe  Asp  Gln  Met  Leu  Lys  His  Arg  Asn  Asp
        65                       70                      75                           80

Asn  Ala  Cys  Gln  Gly  Lys  Gly  Phe  Tyr  Ser  Tyr  Asn  Ala  Phe  Ile  Asn
                           85                      90                           95

Ala  Ala  Arg  Ser  Phe  Pro  Gly  Phe  Gly  Thr  Ser  Gly  Asp  Thr  Thr  Ala
                       100                     105                     110

Arg  Lys  Arg  Glu  Ile  Ala  Ala  Phe  Phe  Ala  Gln  Thr  Ser  His  Glu  Thr
                       115                     120                     125

Thr  Gly  Gly  Trp  Ala  Thr  Ala  Pro  Asp  Gly  Pro  Tyr  Ala  Trp  Gly  Tyr
                  130                     135                     140

Cys  Trp  Leu  Arg  Glu  Gln  Gly  Ser  Pro  Gly  Asp  Tyr  Cys  Thr  Pro  Ser
        145                     150                     155                          160

Gly  Gln  Trp  Pro  Cys  Ala  Pro  Gly  Arg  Lys  Tyr  Phe  Gly  Arg  Gly  Pro
                            165                     170                     175

Ile  Gln  Ile  Ser  His  Asn  Tyr  Asn  Tyr  Gly  Pro  Cys  Gly  Arg  Ala  Ile
                       180                     185                     190

Gly  Val  Asp  Leu  Leu  Asn  Asn  Pro  Asp  Leu  Val  Ala  Thr  Asp  Pro  Val
                  195                     200                     205

Ile  Ser  Phe  Lys  Ser  Ala  Leu  Trp  Phe  Trp  Met  Thr  Pro  Gln  Ser  Pro
             210                     215                     220

Lys  Pro  Ser  Cys  His  Asp  Val  Ile  Ile  Gly  Arg  Trp  Pro  Ser  Ser  Ala
        225                     230                     235                          240

Asp  Arg  Ala  Ala  Asn  Arg  Leu  Pro  Gly  Phe  Gly  Val  Ile  Thr  Asn  Ile
                            245                     250                     255

Ile  Asn  Gly  Gly  Leu  Glu  Cys  Gly  Arg  Gly  Thr  Asp  Ser  Arg  Val  Gln
                       260                     265                     270

Asp  Arg  Ile  Gly  Phe  Tyr  Arg  Arg  Tyr  Cys  Ser  Ile  Leu  Gly  Val  Ser
                       275                     280                     285

Pro  Gly  Asp  Asn  Leu  Asp  Cys  Gly  Asn  Gln  Arg  Ser  Phe  Gly  Asn  Gly
             290                     295                     300

Leu  Leu  Val  Asp  Thr  Met
        305                     310
```

( 2 ) INFORMATION FOR SEQ ID NO:7:

( i ) SEQUENCE CHARACTERISTICS:
        ( A ) LENGTH: 314 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:7:

```
        Thr  Ile  Phe  Ser  Leu  Leu  Phe  Ser  Leu  Leu  Leu  Asn  Ala  Ser  Gly
        1                  5                       10                          15

Ser  Asn  Val  Val  His  Arg  Pro  Asp  Ala  Leu  Cys  Ala  Pro  Gly  Leu  Cys
                       20                      25                      30

Cys  Ser  Lys  Phe  Gly  Trp  Cys  Gly  Asn  Thr  Asn  Asp  Tyr  Cys  Gly  Pro
                  35                      40                      45

Gly  Asn  Cys  Gln  Ser  Gln  Cys  Pro  Gly  Gly  Pro  Gly  Pro  Ser  Gly  Asp
                  50                      55                      60

Leu  Gly  Gly  Val  Ile  Ser  Asn  Ser  Met  Phe  Asp  Gln  Met  Leu  Asn  His
        65                       70                      75                           80

Arg  Asn  Asp  Asn  Ala  Cys  Gln  Gly  Lys  Asn  Asn  Phe  Tyr  Ser  Tyr  Asn
```

|   |   |   |   |   | 85 |   |   |   | 90 |   |   |   | 95 |   |
|---|---|---|---|---|----|---|---|---|----|---|---|---|----|---|

Ala Phe Ile Ser Ala Ala Gly Ser Phe Pro Gly Phe Gly Thr Thr Gly
            100             105             110

Asp Ile Thr Ala Arg Lys Arg Glu Ile Ala Ala Phe Leu Ala Gln Thr
        115             120             125

Ser His Glu Thr Thr Gly Gly Trp Pro Ser Ala Pro Asp Gly Pro Tyr
    130             135             140

Ala Trp Gly Tyr Cys Phe Leu Arg Glu Gln Gly Ser Pro Gly Asp Tyr
145             150             155                         160

Cys Thr Pro Ser Ser Gln Trp Pro Cys Ala Pro Gly Arg Lys Tyr Phe
                165             170             175

Gly Arg Gly Pro Ile Gln Ile Ser His Asn Tyr Asn Tyr Gly Pro Cys
            180             185             190

Gly Arg Ala Ile Gly Val Asp Leu Leu Asn Asn Pro Asp Leu Val Ala
            195             200             205

Thr Asp Ser Val Ile Ser Phe Lys Ser Ala Ile Trp Phe Trp Met Thr
    210             215             220

Pro Gln Ser Pro Lys Pro Ser Cys His Asp Val Ile Thr Gly Arg Trp
225             230             235             240

Pro Ser Gly Ala Asp Gln Ala Ala Asn Arg Val Pro Gly Phe Gly Val
            245             250             255

Ile Thr Asn Ile Ile Asn Gly Gly Leu Glu Cys Gly His Gly Ser Asp
            260             265             270

Ser Arg Val Gln Asp Arg Ile Gly Phe Tyr Arg Arg Tyr Cys Gly Ile
        275             280             285

Leu Gly Val Ser Pro Gly Asp Asn Leu Asp Cys Gly Asn Gln Arg Ser
    290             295             300

Phe Gly Asn Gly Leu Leu Val Asp Thr Val
305             310

( 2 ) INFORMATION FOR SEQ ID NO:8:

( i ) SEQUENCE CHARACTERISTICS:
        ( A ) LENGTH: 330 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:8:

Met Arg Arg His Lys Glu Val Asn Phe Val Ala Tyr Leu Leu Phe Ser
1               5               10              15

Leu Leu Val Leu Val Ser Ala Ala Leu Ala Gln Asn Cys Gly Ser Gln
        20              25              30

Gly Gly Gly Lys Ala Cys Ala Ser Gly Gln Cys Cys Ser Lys Phe Gly
        35              40              45

Trp Cys Gly Asn Thr Asn Asp Tyr Cys Gly Ser Gly Asn Cys Gln Ser
    50              55              60

Gln Cys Pro Gly Gly Gly Pro Gly Pro Gly Gly Asp Leu Gly
65              70              75              80

Ser Ala Ile Ser Asn Ser Met Phe Asp Gln Met Leu Lys His Arg Asn
            85              90              95

Glu Asn Ser Cys Gln Gly Lys Asn Phe Tyr Ser Tyr Asn Ala Phe Ile
            100             105             110

Asn Ala Ala Arg Ser Phe Pro Gly Phe Gly Thr Ser Gly Asp Ile Asn
        115             120             125

Ala Arg Lys Arg Glu Ile Ala Ala Phe Phe Ala Gln Thr Ser His Glu

```
                130                    135                     140
Thr   Thr   Gly   Gly   Trp   Ala   Ser   Ala   Pro   Asp   Gly   Pro   Tyr   Ala   Trp   Gly
145                           150                           155                           160

Tyr   Cys   Phe   Leu   Arg   Glu   Arg   Gly   Asn   Pro   Gly   Asp   Tyr   Cys   Pro   Pro
                        165                           170                           175

Ser   Ser   Gln   Trp   Pro   Cys   Ala   Pro   Gly   Arg   Lys   Tyr   Phe   Gly   Arg   Gly
                  180                           185                                 190

Pro   Ile   Gln   Ile   Ser   His   Asn   Tyr   Asn   Tyr   Gly   Pro   Cys   Gly   Arg   Ala
            195                           200                           205

Ile   Ala   Val   Asp   Leu   Leu   Asn   Asn   Pro   Asp   Leu   Val   Ala   Thr   Asp   Pro
      210                           215                           220

Val   Ile   Ser   Phe   Lys   Thr   Ala   Leu   Trp   Phe   Trp   Met   Thr   Pro   Gln   Ser
225                           230                           235                           240

Pro   Lys   Pro   Ser   Cys   His   Asp   Val   Ile   Ile   Gly   Arg   Trp   Asn   Pro   Ser
                        245                           250                           255

Ser   Ala   Asp   Arg   Ala   Ala   Asn   Arg   Leu   Pro   Gly   Phe   Gly   Val   Ile   Thr
                  260                           265                           270

Asn   Ile   Ile   Asn   Gly   Gly   Leu   Glu   Cys   Gly   Arg   Gly   Thr   Asp   Asn   Arg
            275                           280                           285

Val   Gln   Asp   Arg   Ile   Gly   Phe   Tyr   Arg   Arg   Tyr   Cys   Ser   Ile   Leu   Gly
      290                           295                           300

Val   Thr   Pro   Gly   Asp   Asn   Leu   Asp   Cys   Val   Asn   Gln   Arg   Trp   Phe   Gly
305                           310                           315                           320

Asn   Ala   Leu   Leu   Val   Asp   Val   Asp   Thr   Leu
                        325                           330
```

( 2 ) INFORMATION FOR SEQ ID NO:9:

( i ) SEQUENCE CHARACTERISTICS:
        ( A ) LENGTH: 318 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:9:

```
Ile   Trp   Ser   Val   Gly   Val   Val   Trp   Met   Leu   Leu   Leu   Val   Gly   Gly   Ser
1                       5                       10                              15

Tyr   Gly   Glu   Gln   Cys   Gly   Arg   Gln   Ala   Gly   Gly   Ala   Leu   Cys   Pro   Gly
                  20                            25                        30

Gly   Asn   Cys   Cys   Ser   Gln   Phe   Gly   Trp   Cys   Gly   Ser   Thr   Thr   Asp   Tyr
            35                            40                        45

Cys   Gly   Pro   Gly   Cys   Gln   Ser   Gln   Cys   Gly   Gly   Pro   Ser   Pro   Ala   Pro
      50                            55                      60

Thr   Asp   Leu   Ser   Ala   Leu   Ile   Ser   Arg   Ser   Thr   Phe   Asp   Gln   Met   Leu
65                            70                      75                            80

Lys   His   Arg   Asn   Asp   Gly   Ala   Cys   Pro   Ala   Lys   Gly   Phe   Tyr   Thr   Tyr
                        85                      90                            95

Asp   Ala   Phe   Ile   Ala   Ala   Ala   Lys   Ala   Tyr   Pro   Ser   Phe   Gly   Asn   Thr
                  100                           105                           110

Gly   Asp   Thr   Ala   Thr   Arg   Lys   Arg   Glu   Ile   Ala   Ala   Phe   Leu   Gly   Gln
            115                           120                           125

Thr   Ser   His   Glu   Thr   Thr   Gly   Gly   Trp   Ala   Thr   Ala   Pro   Asp   Gly   Pro
      130                           135                           140

Tyr   Ala   Trp   Gly   Tyr   Cys   Phe   Val   Arg   Glu   Arg   Asn   Pro   Ser   Thr   Cys
145                           150                           155                           160

Ser   Ala   Thr   Pro   Gln   Phe   Pro   Cys   Ala   Pro   Gly   Gln   Gln   Tyr   Tyr   Gly
```

|   |   |   |   |   | 165 |   |   |   |   | 170 |   |   |   |   | 175 |   |
|---|---|---|---|---|---|---|---|---|---|---|---|---|---|---|---|---|

Arg Gly Pro Ile Gln Ile Ser Trp Asn Tyr Asn Tyr Gly Gln Cys Gly
                180                     185                 190

Arg Ala Ile Gly Val Asp Leu Leu Asn Lys Pro Asp Leu Val Ala Thr
            195                 200             205

Asp Ser Val Ile Ser Phe Lys Ser Ala Leu Trp Phe Trp Met Thr Ala
        210             215                 220

Gln Ser Pro Lys Pro Ser Ser His Asp Val Ile Thr Ser Arg Trp Thr
225             230             235                         240

Pro Ser Ser Ala Asp Val Ala Ala Arg Arg Leu Pro Gly Tyr Gly Thr
                245                 250                 255

Val Thr Asn Ile Ile Asn Gly Gly Leu Glu Cys Gly Arg Gly Gln Asp
            260             265                 270

Ser Arg Val Gln Asp Arg Ile Gly Phe Phe Lys Arg Tyr Cys Asp Leu
        275             280                 285

Leu Gly Val Gly Tyr Gly Asn Asn Leu Asp Cys Tyr Ser Gln Thr Pro
        290             295             300

Phe Gly Asn Ser Leu Leu Leu Ser Asp Leu Val Thr Ser Gln
305                 310                 315

(2) INFORMATION FOR SEQ ID NO:10:

(i) SEQUENCE CHARACTERISTICS:
        (A) LENGTH: 43 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:10:

Glu Gln Cys Gly Arg Gln Ala Gly Gly Lys Leu Cys Pro Asn Asn Leu
1               5                   10                  15

Cys Cys Ser Gln Trp Gln Trp Cys Gly Ser Thr Asp Glu Tyr Cys Ser
            20                  25                  30

Pro Asp His Asn Cys Gln Ser Asn Cys Lys Asp
        35                  40

(2) INFORMATION FOR SEQ ID NO:11:

(i) SEQUENCE CHARACTERISTICS:
        (A) LENGTH: 43 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:11:

Gln Gln Cys Gly Arg Gln Lys Gly Gly Ala Leu Cys Ser Gly Asn Leu
1               5                   10                  15

Cys Cys Ser Gln Phe Gly Trp Cys Gly Ser Thr Pro Glu Phe Cys Ser
            20                  25                  30

Pro Ser Gln Gly Cys Gln Ser Arg Cys Thr Gly
        35                  40

(2) INFORMATION FOR SEQ ID NO:12:

(i) SEQUENCE CHARACTERISTICS:
        (A) LENGTH: 43 amino acids
        (B) TYPE: amino acid
        (C) STRANDEDNESS: unknown
        (D) TOPOLOGY: unknown ( i i ) MOLECULE TYPE: protein ( x i ) SEQUENCE DESCRIPTION: SEQ ID NO:12:

| Gln | Gln | Cys | Gly | Arg | Gln | Arg | Gly | Gly | Ala | Leu | Cys | Gly | Asn | Asn | Leu |
|---|---|---|---|---|---|---|---|---|---|---|---|---|---|---|---|
| 1 | | | | 5 | | | | | 10 | | | | | 15 | |

| Cys | Cys | Ser | Gln | Phe | Gly | Trp | Cys | Ser | Ser | Thr | Pro | Glu | Tyr | Cys | Ser |
|---|---|---|---|---|---|---|---|---|---|---|---|---|---|---|---|
| | | | 20 | | | | | 25 | | | | | 30 | | |

| Pro | Ser | Gln | Gly | Cys | Gln | Ser | Gln | Cys | Thr | Gly |
|---|---|---|---|---|---|---|---|---|---|---|
| | | 35 | | | | | 40 | | | |

( 2 ) INFORMATION FOR SEQ ID NO:13:

( i ) SEQUENCE CHARACTERISTICS:
        ( A ) LENGTH: 40 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:13:

| Lys | Cys | Gly | Ser | Gln | Ser | Gly | Gly | Lys | Leu | Cys | Pro | Asn | Asn | Leu | Cys |
|---|---|---|---|---|---|---|---|---|---|---|---|---|---|---|---|
| 1 | | | | 5 | | | | | 10 | | | | | 15 | |

| Cys | Ser | Gln | Trp | Gly | Ser | Cys | Gly | Leu | Gly | Ser | Glu | Phe | Cys | Gly | Gly |
|---|---|---|---|---|---|---|---|---|---|---|---|---|---|---|---|
| | | | 20 | | | | | 25 | | | | | 30 | | |

| Gly | Cys | Gln | Ser | Gly | Ala | Cys | Ser |
|---|---|---|---|---|---|---|---|
| | | 35 | | | | | 40 |

( 2 ) INFORMATION FOR SEQ ID NO:14:

( i ) SEQUENCE CHARACTERISTICS:
        ( A ) LENGTH: 63 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:14:

| Glu | Gln | Cys | Gly | Arg | Gln | Ala | Gly | Gly | Ala | Leu | Cys | Pro | Gly | Gly | Asn |
|---|---|---|---|---|---|---|---|---|---|---|---|---|---|---|---|
| 1 | | | | 5 | | | | | 10 | | | | | 15 | |

| Cys | Cys | Ser | Gln | Phe | Gly | Trp | Cys | Gly | Ser | Thr | Thr | Asp | Tyr | Cys | Gly |
|---|---|---|---|---|---|---|---|---|---|---|---|---|---|---|---|
| | | | 20 | | | | | 25 | | | | | 30 | | |

| Pro | Gly | Cys | Gln | Ser | Gln | Cys | Gly | Gly | Pro | Ser | Pro | Ala | Pro | Thr | Asp |
|---|---|---|---|---|---|---|---|---|---|---|---|---|---|---|---|
| | | 35 | | | | | 40 | | | | | 45 | | | |

| Leu | Ser | Ala | Leu | Ile | Ser | Arg | Ser | Thr | Phe | Asp | Gln | Met | Leu | Lys |
|---|---|---|---|---|---|---|---|---|---|---|---|---|---|---|
| | 50 | | | | | 55 | | | | | 60 | | | |

( 2 ) INFORMATION FOR SEQ ID NO:15:

( i ) SEQUENCE CHARACTERISTICS:
        ( A ) LENGTH: 71 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:15:

| Glu | Gln | Cys | Gly | Ser | Gln | Ala | Gly | Gly | Ala | Arg | Cys | Pro | Ser | Gly | Leu |
|---|---|---|---|---|---|---|---|---|---|---|---|---|---|---|---|
| 1 | | | | 5 | | | | | 10 | | | | | 15 | |

| Cys | Cys | Ser | Lys | Phe | Gly | Trp | Cys | Gly | Asn | Thr | Asn | Asp | Tyr | Cys | Gly |
|---|---|---|---|---|---|---|---|---|---|---|---|---|---|---|---|
| | | | 20 | | | | | 25 | | | | | 30 | | |

| Pro | Gly | Asn | Cys | Gln | Ser | Gln | Cys | Pro | Gly | Gly | Pro | Thr | Pro | Thr | Pro |
|---|---|---|---|---|---|---|---|---|---|---|---|---|---|---|---|
| | | 35 | | | | | 40 | | | | | 45 | | | |

```
      Pro  Thr  Pro  Pro  Gly  Gly  Gly  Asp  Leu  Gly  Ser  Ile  Ile  Ser  Ser  Ser
           50                  55                            60

Met  Phe  Asp  Gln  Met  Leu  Lys
      65                  70
```

(2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:16:

```
      Gln  Gly  Ile  Gly  Ser  Ile  Val  Thr  Ser  Asp  Leu  Phe  Asn  Glu  Met  Leu
      1                  5                            10                           15

Lys
```

(2) INFORMATION FOR SEQ ID NO:17:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:17:

```
      Gln  Gly  Ile  Gly  Ser  Ile  Val  Thr  Asn  Asp  Leu  Phe  Asn  Glu  Met  Leu
      1                  5                            10                           15

Lys
```

(2) INFORMATION FOR SEQ ID NO:18:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

GTATGTAAAA AG          12

(2) INFORMATION FOR SEQ ID NO:19:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

TGGGAGCAGC GG          12

(2) INFORMATION FOR SEQ ID NO:20:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

TACTCTGTGT GATGA      15

( 2 ) INFORMATION FOR SEQ ID NO:21:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

TACTTGTGTG ATGA      14

( 2 ) INFORMATION FOR SEQ ID NO:22:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

AATTTTTTAA      10

( 2 ) INFORMATION FOR SEQ ID NO:23:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

TTAAAAAATT      10

( 2 ) INFORMATION FOR SEQ ID NO:24:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear -continued (ii) MOLECULE TYPE: DNA (genomic)

(iii) HYPOTHETICAL: NO (iv) ANTI-SENSE: NO (xi) SEQUENCE DESCRIPTION: SEQ ID NO:24:

TCCCCAAGGT 10

(2) INFORMATION FOR SEQ ID NO:25:

(i) SEQUENCE CHARACTERISTICS:
 (A) LENGTH: 10 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

TGGAACCCCT 10

(2) INFORMATION FOR SEQ ID NO:26:

(i) SEQUENCE CHARACTERISTICS:
 (A) LENGTH: 16 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

ATGCATGCAT ATGCAT 16

That which is claimed is:

1. An isolated DNA comprising a promoter obtained from a monocotyledonous plant, said DNA characterized as being responsive to physical and/or biological stress; and comprising the same sequence as nucleotides 1836 to about 1884, as set forth in Sequence ID No. 1.

2. A DNA according to claim 1 further comprising, as part of the same contiguous fragment, the same sequence as nucleotides 1-76, as set forth in Sequence ID No. 2.

3. A DNA according to claim 1 further characterized by comprising the same sequence as nucleotides 1810 to about 1884, as set forth in Sequence ID No. 1.

4. A DNA according to claim 3 further comprising, as part of the same contiguous fragment, the same sequence as nucleotides 1-76, as set forth in Sequence ID No. 2.

5. A DNA according to claim 1 further characterized by comprising the same sequence as nucleotides 1724 to about 1884, as set forth in Sequence ID No. 1.

6. A DNA according to claim 5 further comprising, as part of the same contiguous fragment, the same sequence as nucleotides 1-76, as set forth in Sequence ID No. 2.

7. A DNA construct comprising the promoter of claim 1 operatively linked to at least one heterologous reporter gene.

8. A DNA construct according to claim 7 wherein said reporter gene is selected from chloramphenicol acetyltransferase, $\beta$-glucuronidase, $\beta$-lactamase, or firefly luciferase.

9. Plant material containing the DNA construct of claim 7.

10. An isolated recombinant DNA construct comprising the monocotyledon promoter of claim 1 operatively linked to at least one heterologous structural gene.

11. A DNA construct according to claim 10 wherein said heterologous structural gene is selected from the Bacillus thuringensis toxin gene, genes encoding enzymes involved in phytoalexin biosynthesis, proteinase inhibitor genes, lytic enzyme genes, genes encoding fungal elicitors, or genes encoding inducers of plant disease resistance mechanisms.

12. Plant material containing the DNA construct of claim 10.

13. A method for inducing the expression of heterologous, functional gene(s) in monocotyledon and dicotyledon plants, said method comprising:
 subjecting the plant material of claim 12 to conditions which induce transcription of said DNA construct.

* * * * *